United States Patent
Fuchs

[11] Patent Number: 6,002,010
[45] Date of Patent: Dec. 14, 1999

[54] CARBOXYLIC ACID DERIVATIVE PREPARATION PROCESS

[75] Inventor: Eberhard Fuchs, Frankenthal, Germany

[73] Assignee: BASF Aktiengesellschaft, Ludwigshafen, Germany

[21] Appl. No.: 08/952,239

[22] PCT Filed: May 7, 1996

[86] PCT No.: PCT/EP96/01890

§ 371 Date: Nov. 10, 1997

§ 102(e) Date: Nov. 10, 1997

[87] PCT Pub. No.: WO96/36592

PCT Pub. Date: Nov. 21, 1996

[30] Foreign Application Priority Data

May 19, 1995 [DE] Germany .................. 195 18 474

[51] Int. Cl.⁶ .................................................. C07D 213/56
[52] U.S. Cl. .................. 546/265; 546/257; 546/262; 546/264; 546/279.4; 554/68; 554/157; 564/126; 564/130; 560/179; 560/215
[58] Field of Search ............. 554/68, 157; 544/106, 544/102, 108, 300, 400; 564/124, 130; 546/245, 264, 257, 262, 265, 274.4; 560/179, 215

[56] References Cited

U.S. PATENT DOCUMENTS

| | | | |
|---|---|---|---|
| 3,957,804 | 5/1976 | Ishioka et al. | 260/295 |
| 4,613,684 | 9/1986 | Aayoma et al. | 560/179 |
| 4,987,256 | 1/1991 | Ebata et al. | 564/126 |
| 5,103,055 | 4/1992 | Cesa | 564/130 |

FOREIGN PATENT DOCUMENTS

| | | |
|---|---|---|
| 392 361 | 10/1990 | European Pat. Off. . |
| 412 310 | 2/1991 | European Pat. Off. . |
| 561 614 | 9/1993 | European Pat. Off. . |
| 2539435 | 9/1975 | Germany . |
| 2714767 | 4/1977 | Germany . |
| 43 39648 | 11/1993 | Germany . |
| 96/16039 | 5/1996 | WIPO . |

OTHER PUBLICATIONS

*Chem. Abst.*, vol. 78, No. 5, 1973.

Primary Examiner—Deborah D Carr
Attorney, Agent, or Firm—Keil & Weinkauf

[57] ABSTRACT

A process for preparing carboxylic acid derivatives of the formula I $$R^1-\overset{O}{\underset{\|}{C}}-X, \quad (I)$$

where
X is $OR^2$ or $NH_2$,
$R^1$ is $C_1-C_{20}$-alkyl, $C_1-C_{20}$-hydroxyalkyl, $C_3-C_{12}$-cycloalkyl, $C_4-C_{12}$-alkylcycloalkyl, $C_4-C_{12}$-cycloalkylalkyl, $C_5-C_{20}$-alkylcycloalkylalkyl, aryl, $C_7-C_{20}$-aralkyl, $C_7-C_{20}$-alkylaryl, a heteroaliphatic or heteroaromatic ring with 5 to 8 carbon atoms and
$R^2$ is $C_1-C_{20}$-alkyl,
from carbonitriles of the formula II $$R^1-C\equiv N \quad (II),$$

where $R^1$ has the abovementioned meanings, and alcohols of the formula III $$R^2-OH \quad (III),$$

where $R^2$ has the abovementioned meanings, at from 50 to 300° C. under from 0.1 to 350 bar in the presence of a heterogeneous catalyst, wherein the reaction is carried out in liquid phase.

7 Claims, No Drawings

CARBOXYLIC ACID DERIVATIVE PREPARATION PROCESS

This application is a 371 of PCT/EP96/01890 filed May 7, 1996

BACKGROUND OF THE INVENTION

1. Field of the Invention

The invention relates to a process for preparing carboxylic acid derivatives from carbonitriles and alcohols at elevated temperatures on titanium oxide catalysts.

2. Description of the Related Art

DE-A 27 14 767 discloses a process for preparing carboxylic acid derivatives by gas-phase reaction of nitrites with alcohols and water on solid, metal-containing catalysts such as copper, zinc, chromium, bismuth, manganese, iron, nickel, cadmium on carriers such as $Al_2O_3$, $SiO_2$, $ZrO_2$ or $TiO_2$. Dehydration and etherification are found as side reactions.

EP-A 412 310, for example, discloses a process for preparing carboxamides by hydration of nitrites with water on manganese-containing catalysts, which can subsequently be reacted with alcohols by acid catalysis, in the presence of metal salts, eg. as disclosed in U.S. Pat. No. 4,613,684, or in the gas phase on solid catalysts, eg. as disclosed in EP-A 561 614, or with formic ester resulting in formamide formation, eg. as disclosed in EP-A 392 361, on metal oxides to give the carboxylic acid derivatives.

The disadvantages for industrial application are the two stages and the formation of byproducts, such as production of salt or formamide formation.

DE-A 43 39 648 discloses a process for preparing caprolactam (a cyclic amide) by reacting aminocapronitrile with water in an ethanolic solution on a titanium oxide catalyst.

BRIEF SUMMARY OF THE INVENTION

We have found that the above mentioned disadvantages of the prior art processes are overcome by a novel and improved process for preparing carboxylic acid derivatives of the formula I

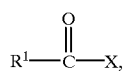
(I)

where

X is $OR^2$ or $NH_2$, $R^1$ is $C_1$–$C_{20}$-alkyl, $C_1$–$C_{20}$-hydroxyalkyl, $C_3$–$C_{12}$-cycloalkyl, $C_4$–$C_{12}$-alkylcycloalkyl, $C_4$–$C_{12}$-cycloalkylalkyl, $C_5$–$C_{20}$-alkylcycloalkylalkyl, aryl, $C_7$–$C_{20}$-aralkyl, $C_7$–$C_{20}$-alkylaryl, a heteroaliphatic or heteroaromatic ring with 5 to 8 carbon atoms and $R^2$ is $C_1$–$C_{20}$-alkyl, from carbonitriles of the formula II

$R^1$—C≡N (II), where $R^1$ has the abovementioned meanings, and alcohols of the formula III

$R^2$—OH (III), where $R^2$ has the abovementioned meanings, at from 50 to 300° C. under from 0.1 to 350 bar in the presence of a heterogeneous catalyst, wherein the reaction is carried out in liquid phase.

DETAILED DESCRIPTION OF THE INVENTION

The process according to the invention can be carried out in the following way:

The carbonitrile II can be brought into contact with an alcohol III, preferably dissolved in the alcohol III, at from 50 to 300° C., preferably 100 to 290° C., particularly preferably 140 to 270° C., under from 0.1 to 350 bar, preferably 1 to 200 bar, particularly preferably 30 to 140 bar, in liquid phase with a titanium oxide catalyst, as a rule in pressure-stable apparatus such as autoclaves and tubular reactors, preferably tubular reactors. The result is, as a rule, an alcoholic solution of the carboxylic ester and of the carboxamide I, from which the carboxylic ester and the carboxamide I can be obtained by conventional methods, for example by distillation, extraction or crystallization.

The carboxamide can be returned to the reactor together with fresh carbonitrile II.

The reaction of solid carbonitriles II or solid alcohols III can be carried out in inert solvents, for example in ethers, preferably ethers with 2 to 20 carbon atoms, particularly preferably ethers with 4 to 12 carbon atoms, such as diethyl ether, methyl tert-butyl ether or tetrahydrofuran, hydrocarbons, preferably hydrocarbons with 5 to 30 carbon atoms, particularly preferably hydrocarbons with 5 to 12 carbon atoms, such as toluene and xylene or, advantageously, in the appropriate carboxylic ester I.

Examples of suitable heterogeneous catalysts are acidic, basic or amphoteric oxides of elements of groups IIA, IIIA, IVA of the Periodic Table of the Elements, such as calcium oxide, magnesium oxide, boron oxide, aluminum oxide, tin oxide or silicon dioxide, pyrogenic silica, as silica gel, kieselguhr, quartz, furthermore oxides of metals of groups IIB, IIIB, IVB, VB, VIB and VIIB of the Periodic Table of the Elements, such as titanium oxide, especially titanium dioxide, eg. amorphous, as anatase or rutile, zirconium oxide, zinc oxide, manganese oxide, vanadium oxide, niobium oxide, iron oxide, chromium oxide, molybdenum oxide, tungsten oxide, oxides of the lanthanides and actinides such as cerium oxide, thorium oxide, praseodymium oxide, samarium oxide, rare earth mixed oxides or mixtures thereof. Some sulfides, selenides and tellurides such as zinc telluride, tin selenide, molybdenum sulfide, tungsten sulfide, sulfides of nickel, zinc and chromium, can also be used.

The abovementioned compounds can be doped with compounds of groups IA, IIA, IIIA, IVA, VA, VIA and VIIA of the Periodic Table of the Elements or contain the later.

Further suitable catalysts are zeolites, phosphate and heteropolyacids, and acidic and alkaline ion exchangers such as Naphion.

These catalysts may, where appropriate, in each case contain up to 50% by weight of copper, tin, zinc, manganese, iron, cobalt, nickel, ruthenium, palladium, platinum, silver or rhodium.

The catalysts can, depending on the composition of the catalyst, be used as unsupported or supported catalyst. Thus, for example, titanium dioxide can be used as titanium dioxide pellets or as titanium dioxide applied in a thin layer to a support. The methods used for applying $TiO_2$ to a support such as silicon dioxide, aluminum oxide or zirconium dioxide can be all those described in the literature. Thus, a thin $TiO_2$ layer can be appLied by hydrolyzing organotitanium compounds such as titanium isopropoxide or butoxide or by hydrolyzing $TiCl_4$ or other inorganic Ti-containing compounds. It is also possible to use brines containing titanium oxide.

The reaction can be carried out, for example, in suspension, preferably in a fixed bed. The reaction is preferably carried out in a fixed bed because this makes it easy to carry out continuously, the yields and selectivities in the fixed bed are, as a rule, very high and thus result in short holdup times with very high throughputs. Since the heterogeneous catalysts used have, according to observations to date, a long useful life, the consumption of catalyst is extremely low.

The substituents X, $R^1$ and $R^2$ in the compounds I, II and III have the following meanings:

X $OR^2$ $NH_2$ $R^1, R^2$ $C_1$–$C_{20}$-alkyl, preferably $C_1$–$C_{12}$-alkyl, particularly preferably $C_1$–$C_8$-alkyl such as methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl and isooctyl, especially $C_1$–$C_4$-alkyl such as methyl, ethyl, n-propyl, isopropyl, n-butyl, isobutyl, sec-butyl and tert-butyl, $C_1$–$C_{20}$-hydroxyalkyl, preferably $C_1$–$C_8$-hydroxyalkyl, particularly preferably $C_1$–$C_4$-hydroxyalkyl such as hydroxymethyl, 1-hydroxyethyl, 2-hydroxyethyl and 1-methyl-1-hydroxyethyl, $C_3$–$C_{12}$-cycloalkyl, preferably $C_5$–$C_8$-cycloalkyl such as cyclopentyl, cyclohexyl, cycloheptyl and cyclooctyl, particularly preferably cyclopentyl and cyclohexyl, $C_4$–$C_{12}$-alkylcycloalkyl, preferably $C_5$–$C_{10}$-alkylcycloalkyl, particularly preferably $C_5$–$C_8$-alkylcycloalkyl, $C_4$–$C_{12}$-cycloalkylalkyl, preferably $C_5$–$C_{10}$-cycloalkylalkyl, particularly preferably $C_5$–$C_8$-cycloalkylalkyl, $C_5$–$C_{20}$-alkylcycloalkylalkyl, preferably $C_6$–$C_{16}$-alkylcycloalkylalkyl, particularly preferably $C_7$–$C_{12}$-alkylcycloalkylalkyl, aryl such as phenyl, 1-naphthyl and 2-naphthyl, preferably phenyl, $C_7$–$C_{20}$-alkylaryl, preferably $C_7$–$C_{16}$-alkylaryl, [lacuna] preferably $C_7$–$C_{12}$-alkylphenyl such as 2-methylphenyl, 3-methylphenyl, 4-methylphenyl, 2-ethylphenyl, 3-ethylphenyl and 4-ethylphenyl, $C_7$–$C_{20}$-aralkyl, preferably $C_7$–$C_{16}$-aralkyl, [lacuna] preferably $C_7$–$C_{12}$-phenalkyl [sic] such as phenylmethyl, 1-phenylethyl and 2-phenylethyl, a heteroaliphatic ring with 5 to 8 carbon atom such as 2-morpholinyl, 3-morpholinyl, 2-piperidinyl, 3-piperidinyl and 4-piperidinyl, a heteroaromatic ring with 5 to 8 carbon atoms such as 2-pyridyl, 3-pyridyl, 4-pyridyl, 2-pyrazolyl, 2-imidazolyl, 4(5)-imidazolyl, preferably 3-pyridyl.

The carboxylic esters and carboxamides I are suitable as intermediates, plastics precursors and in crop protection and pharmacy.

EXAMPLES

Example 1

A 20% by weight ethanolic solution of nicotinonitrile was passed with the addition of 1 mol of water (3.5% by weight based on the solution) at 220° C. and 80 bar through a tube packed with titanium oxide (1.5 mm pellets). The holdup time was set variably via the flow rate.

The composition of the discharge from the reaction is summarized in Table 1.

TABLE 1

| Holdup time | Nicotino-nitrile | Ethyl nicotinate | Nicotin-amide | Others |
|---|---|---|---|---|
| [min] | [%] | [%] | [%] | [%] |
| 15 | 5.1 | 5.4 | 9.4 | 0.1 |
| 30 | 1.9 | 8.6 | 9.1 | 0.4 |
| 60 | 0.6 | 11.3 | 7.4 | 0.7 |

Example 2

A 20% by weight ethanolic solution of nicotinonitrile was pumped as in Example 1 in the presence of 1 mol of water at 220° C. at 80 bar through an empty tube. No reaction took place.

We claim:

1. A process for preparing carboxylic acid derivatives of the formula I

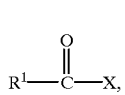

(I)

where

X is $OR^2$ or $NH_2$, $R^1$ is $C_1$–$C_{20}$-alkyl, $C_1$–$C_{20}$-hydroxyalkyl, $C_3$–$C_{12}$-cycloalkyl, $C_4$–$C_{12}$-alkylcycloalkyl, $C_4$–$C_{12}$-cycloalkylalkyl, $C_5$–$C_{20}$-alkylcycloalkylalkyl, aryl, $C_7$–$C_{20}$-aralkyl, $C_7$–$C_{20}$-alkylaryl, a heteroaliphatic or heteroaromatic ring with 5 to 8 carbon atoms and $R^2$ is $C_1$–$C_{20}$-alkyl, from carbonitriles of the general formula II

where $R^1$ has the abovementioned meanings, and alcohols of the formula III

where $R^2$ has the abovementioned meanings, at from 50 to 300° C. under from 0.1 to 350 bar in the presence of titanium dioxide as a heterogeneous catalyst, wherein the reaction is carried out in liquid phase.

2. The process of claim 1, wherein anatase, rutile or mixtures thereof is used as titanium dioxide.

3. The process of claim 1, wherein the reaction is carried out at from 100 to 290° C.

4. The process of claim 1, wherein the reaction is carried out at from 140 to 270° C.

5. The process of claim 1, wherein the reaction is carried out in liquid phase under from 1 to 200 bar.

6. The process of claim 1, wherein the reaction is carried out under from 30 to 140 bar.

7. The process of claim 1, wherein $R^1$ is 3-pyridyl, 1-methyl-1-hydroxyethyl, 1-hydroxyethyl or 2-hydroxyethyl.

* * * * *